(12) United States Patent
McLaughlin et al.

(10) Patent No.: US 10,961,213 B2
(45) Date of Patent: Mar. 30, 2021

(54) PROCESS FOR PREPARATION OF BENZYLIC AMIDES

(71) Applicant: BASF SE, Ludwigshafen am Rhein (DE)

(72) Inventors: Martin John McLaughlin, Ludwigshafen (DE); Karsten Koerber, Ludwigshafen (DE); Birgit Gockel, Navi Mumbai (IN); Devendra Vyas, Research Triangle Park, NC (US); Arun Narine, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/480,407

(22) PCT Filed: Jan. 16, 2018

(86) PCT No.: PCT/EP2018/050937
§ 371 (c)(1),
(2) Date: Jul. 24, 2019

(87) PCT Pub. No.: WO2018/137959
PCT Pub. Date: Aug. 2, 2018

(65) Prior Publication Data
US 2019/0382362 A1    Dec. 19, 2019

(30) Foreign Application Priority Data

Jan. 25, 2017  (IN) .............................. 201721002825
Feb. 10, 2017  (EP) ..................................... 17155685

(51) Int. Cl.
*C07D 307/79*       (2006.01)
(52) U.S. Cl.
CPC .................................. *C07D 307/79* (2013.01)
(58) Field of Classification Search
None
See application file for complete search history.

(56) References Cited

U.S. PATENT DOCUMENTS

2018/0215740 A1   8/2018  Datta et al.
2019/0055200 A1   2/2019  Klauber et al.

FOREIGN PATENT DOCUMENTS

WO    WO-2008/122375 A2   10/2008
WO    WO-2010/027051 A1    3/2010
(Continued)

OTHER PUBLICATIONS

"Methoden der organischen Chemie", Houben-Weyl, vol. E5, 1985, pp. 957-959.
(Continued)

*Primary Examiner* — Samantha L Shterengarts
(74) *Attorney, Agent, or Firm* — Marshall, Gerstein & Borun LLP

(57) ABSTRACT

The present invention relates to a process for preparing benzylic amides of formula I

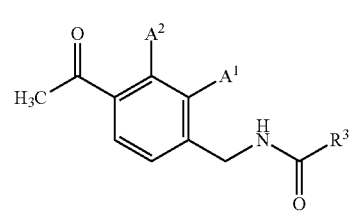

wherein the variables have the meaning as defined in the description, by reductive amidation of a nitrile of formula II

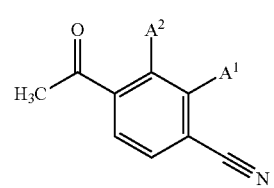

wherein the variables have the meanings given for formula I, with an activated carbonyl compound of formula III,

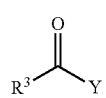

and which nitrile is obtained by reaction of a compound of formula IV

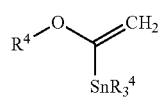

with a halogen compound of formula V,

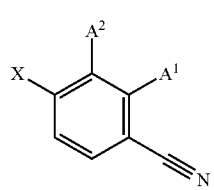

(Continued)

wherein X is a halogen atom, preferably bromo, which halogen compound V in turn is obtained by Sandmeyer reaction of an aniline derivative of formula VI

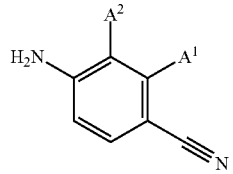

VI novel compounds of formula I, and processes for preparing compounds of formula XII

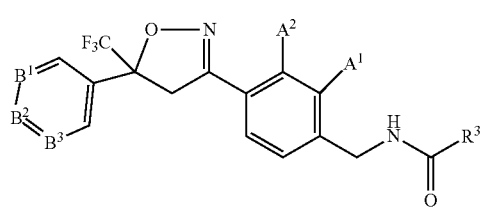

XII wherein the variables have the meaning as defined in the description by condensing compounds of formula I with compounds of formula X

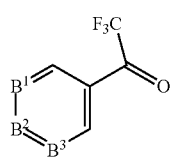

X and subjecting the resulting α,β-unsaturated ketone of formula XI

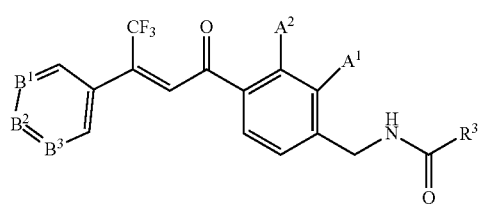

XI to a reaction with hydroxylamine to yield compounds of formula XII.

6 Claims, No Drawings

(56) References Cited

FOREIGN PATENT DOCUMENTS

| WO | WO-2011/003793 A1 | 1/2011 |
| WO | WO-2011/054436 A2 | 5/2011 |
| WO | WO-2011/161130 A1 | 12/2011 |
| WO | WO-2012/158396 A1 | 11/2012 |
| WO | WO-2013/092943 A1 | 6/2013 |
| WO | WO-2013/185103 A1 | 12/2013 |
| WO | WO-2014/001120 A1 | 1/2014 |
| WO | WO-2014/019609 A1 | 2/2014 |
| WO | WO-2015/091045 A1 | 6/2015 |
| WO | WO-2015/104422 A1 | 7/2015 |
| WO | WO-2016/102482 A1 | 6/2016 |
| WO | WO-2017/012938 A1 | 1/2017 |
| WO | WO-2017/016883 A1 | 2/2017 |
| WO | WO-2017/133942 A1 | 8/2017 |
| WO | WO-2018/082962 A1 | 5/2018 |
| WO | WO-2018/082964 A1 | 5/2018 |

OTHER PUBLICATIONS

"The Stille Reaction", Organic Reactions, vol. 50, 1997, pp. 12-15, 27-30, 52-60 and p. 372.

Beller, et al., "Progress in hydroformylation and carbonylation", Journal of Molecular Catalysis A: Chemical, vol. 104, Issue 1, Dec. 5, 1995, pp. 17-85.

Cabri, et al., ".alpha.—Regioselectivity in palladium-catalyzed arylation of acyclic enol ethers", The Journal of Organic Chemistry, vol. 57, Issue 5, 1992, pp. 1481-1486.

Cabri, et al., "Palladium-catalyzed a-arylation of vinyl butyl ether with aryl halides", Tetrahedron Letters, vol. 32, Issue 14, Apr. 1, 1991, pp. 1753-1756.

Cabri, et al., "Recent Developments and New Perspectives in the Heck Reaction", Accounts of Chemical Research, vol. 28, Issue 1, 1995, pp. 2-7.

Dai, et al., The First General Method for Palladium-Catalyzed Negishi Cross-Coupling of Aryl and Vinyl Chlorides: Use of Commercially Available Pd(P(t-Bu)3)2 as a Catalyst, Journal of the American Chemical Society, vol. 123, Issue 12, 2001, vol. 2719-2724.

European Search Report for EP Patent Application No. 17155685.5, dated May 11, 2017, 4 pages.

Hodgson, The Sandmeyer Reaction, Chemical Reviews, vol. 40, Issue 2, 1947, pp. 251-277.

International Search Report for PCT Patent Application No. PCT/EP2018/050937, dated Mar. 21, 2018, 4 pages.

Krasovskiy, et al., "A LICIMediated Br/Mg Exchange Reaction for the Preparation of Functionalized Aryl and Heteroarylmagnesium Compounds from Organic Bromides", Angewandte Chemie, vol. 43, Issue 25, Jun. 21, 2004, pp. 3333-3336.

Krasovskiy, et al., "Highly Efficient Reagents for Br/Mg Exchange", Angewandte Chemie, vol. 45, Issue 1, Dec. 16, 2005, pp. 159-162.

Mee, et al., "Stille Coupling Made Easier—The Synergic Effect of Copper(I) Salts and the Fluoride Ion", Angewandte Chemie, vol. 43, Issue 9, Feb. 20, 2004, pp. 1132-1136.

Netherton, et al., "Air-Stable Trialkylphosphonium Salts: Simple, Practical, and Versatile Replacements for Air-Sensitive Trialkylphosphines. Applications in Stoichiometric and Catalytic Processes", Organic Letters, vol. 3, Issue 26, 2001, pp. 4295-4298.

Orchin, "The Grignard reagent: Preparation, structure, and some reactions", Journal of Chemical Education, vol. 66, Issue 7, 1989, pp. 586-588.

Otsuka, et al., "Bis(tertiary phosphine)palladium(0) and -platinum(0) complexes: preparations and crystal and molecular structures", Journal of the American Chemical Society, vol. 98, Issue 19, 1976, pp. 5850-5858.

Parker, et al., "Isoquinoline quinones. Preparation of saframycin intermediates and a total synthesis of mimosamycin", The Journal of Organic Chemistry, vol. 53, Issue 12, 1988, pp. 2847-2850.

Stanforth, "Compounds with Two Carbon-Heteroatom Bonds", Science of Synthesis, vol. 31, 2007, 2 pages.

Stanforth, "Compounds with Two Carbon-Heteroatom Bonds", Science of Synthesis, vol. 31, 2007, 3 pages.

Subramanian, "Compounds with Four and Three Carbon-Heteroatom Bonds", Science of Synthesis, vol. 19, 2004, 6 pages.

Waldvogel, et al., "Compounds with Two Carbon-Heteroatom Bonds", Science of Synthesis, vol. 31, 2007, 1 page.

(56) References Cited

OTHER PUBLICATIONS

Waldvogel, et al., "Compounds with Two Carbon-Heteroatom Bonds", Science of Synthesis, vol. 31, 2007, 2 pages.
Waldvogel, et al., "Compounds with Two Carbon-Heteroatom Bonds", Science of Synthesis, vol. 31, 2007, 3 pages.
Yoshida, et al., "Reactions of two-coordinate phosphine platinum(0) and palladium(0) compounds. Ligand exchange and reactivities toward small molecules", Journal of the American Chemical Society, vol. 99, Issue 7, 1977, pp. 2134-2140.

PROCESS FOR PREPARATION OF BENZYLIC AMIDES

This application is a National Stage application of International Application No. PCT/EP2018/050937, filed Jan. 16, 2018. This application also claims priority under 35 U.S.C. § 119 to Indian Patent Application No. 201721002825, filed Jan. 25, 2017 and European Patent Application No. 17155685.5, filed Feb. 10, 2017.

The present invention relates to a process for preparing benzylic amides of formula I

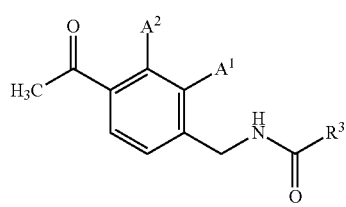

wherein
$A^1$ is halogen, $C_1$-$C_4$-alkyl, $C_1$-$C_4$-haloalkyl, $C_1$-$C_4$-alkoxy, or $C_1$-$C_4$-haloalkoxy;
$A^2$ is H, or $C_1$-$C_4$-alkyl;
or $A^1$ and $A^2$ together form a chain \$-$(CH_2)_m$—O-#, or —$(CH_2)_m$—, wherein # is the bond to position $A^1$, and \$ is the bond to position $A^2$;
m is 2, 3, or 4;
$R^3$ is H, $C_1$-$C_6$-alkyl, $C_1$-$C_6$-haloalkyl, wherein the carbon chains may be substituted with one or more $R^{31}$; $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl which is unsubstituted or substituted with CN, $C_3$-$C_6$-halocycloalkyl, $N(R^{5a})R^{5b}$, $C(=O)N(R^{5a})R^{5b}$, $CH=NOR^4$, phenyl, or a 4-, 5-, or 6-membered saturated, partially or fully unsaturated heterocyclic ring (HET) comprising 1, 2 or 3 heteroatoms N, O, and/or S as ring members, which rings are unsubstituted or partially or fully substituted with same or different $R^{32}$,
$R^{31}$ is OH, CN, $C_3$-$C_6$-cycloalkyl unsubstituted or substituted with CN or halomethyl, $C_3$-$C_6$-halocycloalkyl, $C_1$-$C_6$-alkoxy, $C_1$-$C_6$-haloalkoxy, $SO_n$—$C_1$-$C_6$-alkyl, $SO_n$—$C_1$-$C_6$-haloalkyl, $C(=O)N(R^{5a})R^{5b}$, phenyl, or a 4-, 5-, or 6-membered saturated, partially or fully unsaturated heterocyclic ring (HET) comprising 1, 2 or 3 heteroatoms N, O, and/or S as ring members, which rings are unsubstituted or partially or fully substituted with same or different $R^{32}$;
$R^{32}$ is halogen, CN, $NO_2$, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $SO_n$—$C_1$-$C_4$-alkyl, $SO_n$—$C_1$-$C_4$-haloalkyl, $C_1$-$C_4$-alkylcarbonyl, $C_1$-$C_4$-haloalkylcarbonyl, aminocarbonyl, $C_1$-$C_4$-alkylaminocarbonyl, and di-($C_1$-$C_4$-alkyl)aminocarbonyl; or
two $R^{32}$ present on the same carbon atom of a saturated ring may form together =O or =S; or
two $R^{32}$ present on the same S or SO ring member of a heterocycle may together form a group =N($C_1$-$C_6$-alkyl), =NO($C_1$-$C_6$-alkyl), =NN(H)($C_1$-$C_6$-alkyl) or =NN($C_1$-$C_6$-alkyl)$_2$;
$R^4$ is H, $C_1$-$C_6$-alkyl, or $C_1$-$C_6$-haloalkyl;
$R^{5a}$ is H, or $C_1$-$C_6$-alkyl;
$R^{5b}$ is H, $C_1$-$C_6$-alkyl, $C_1$-$C_6$-haloalkyl, $C_2$-$C_4$-alkenyl, $C_2$-$C_4$-alkynyl, $CH_2CN$, $C_3$-$C_6$-cycloalkyl, $C_3$-$C_6$-halocycloalkyl, $C_3$-$C_6$-cycloalkylmethyl, $C_3$-$C_6$-halocycloalkylmethyl, phenyl, heterocycle HET which rings are unsubstituted or partially or fully substituted with same or different $R^{32}$;
each n is independently 0, 1, or 2;
by reductive amidation of a nitrile of formula II

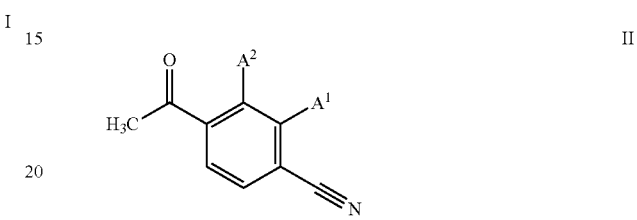

wherein the variables have the meanings given for formula I, with an activated carbonyl compound of formula III,

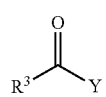

wherein $R^3$ is as defined above, and Y is a nucleophilic leaving group, and which nitrile is obtained by reaction of a compound of formula IV or IVa

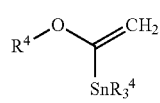

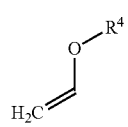

with a halogen compound of formula V,

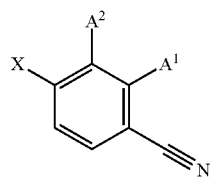

wherein X is a halogen atom, preferably bromo, which halogen compound V in turn is obtained by Sandmeyer reaction of an aniline derivative of formula VI

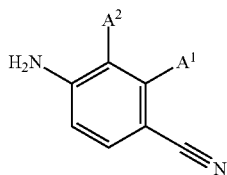

The aniline derivative of formula VI is known, commercially available, or can be prepared by known methods, but can be advantageously be prepared by reductive dehalogenation of the chloro compound of formula VII

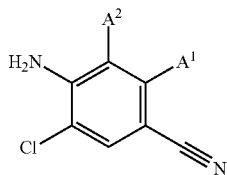

which can be prepared from an amide of formula VII

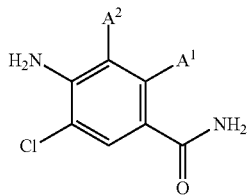

which can be prepared by amidation of the corresponding benzoic acid of formula IX

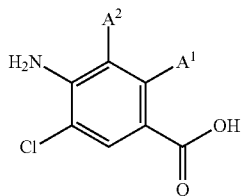

Preparation of compounds of formula VI starting from formula IX is particularly advantageous for compounds wherein $A^1$ and $A^2$ together form a chain $-CH_2CH_2O-\#$. This is because 4-amino-5-chloro-2,3-dihydrobenzofuran-7-carboxylic acid is technically available in large scale and hence a suitable starting material for a technical manufacture of formula I intermediates, and further chemicals derived therefrom.

In addition, the invention relates to novel compounds of formula I. These compounds are valuable intermediates in fine chemistry, and are useful for the preparation of pharmaceutical and pesticidal active compounds. The invention furthermore relates to a process for preparing active compounds of formula XII by condensation of compounds I with compounds of formula X via an intermediate of formula XI.

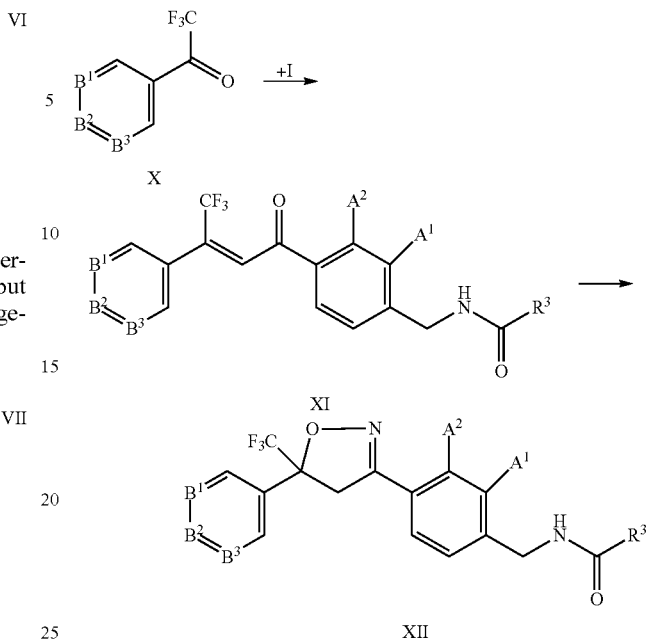

In formulae X, XI, and XII the variables have following meaning:
$B^1$, $B^2$ and $B^3$ are each independently selected from N and $CR^2$, with the proviso that at most two of $B^1$, $B^2$, and $B^3$ are N; and
each $R^2$ is independently H, halogen, CN, halogen, $C_1$-$C_2$-haloalkoxy, or $C_1$-$C_2$-haloalkyl;
and the other variables are as defined for formula I.

Compounds of formula XII in general and their pesticidal activity are known from WO 2016/102482. In view of the methods for preparing the compounds of formula I known from the aforementioned art, there is a need for a more efficient process for preparing the compounds of formula I which is applicable to technical scale manufacture. The present invention provides a highly efficient route to manufacture these compounds.

The reductive amidation of the nitrile of formula II is effected with an activated carbonyl compound of formula III wherein Y is a nucleophilic leaving group such as halogen or $OC(=O)R^3$, under basic conditions in the presence of hydrogen.

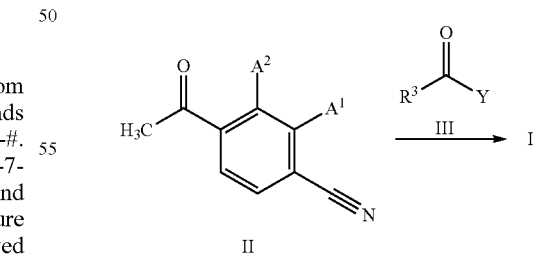

This transformation is usually carried out at temperatures of from −50° C. to 150° C., preferably from −10° C. to 50° C., in an inert solvent, in the presence of a base and a catalyst [cf. J. Org. Chem. 1988, 53, 2847].

Suitable solvents are aliphatic hydrocarbons, aromatic hydrocarbons such as toluene, o-, m-, and p-xylene, ethers such as diethylether, diisopropylether, tert.-butylmethylether (MTBE), dioxane, anisole, and tetrahydrofurane (THF), esters such as ethyl acetate, methyl acetate, isopropyl acetate, alcohols such as methanol, ethanol, n-propanol, isopropanol, n-butanol, and tert.-butanol, moreover dimethyl formamide (DMF), and dimethylacetamide (DMA), acids such as acetic acid, and water, preferably ethers and alcohols. It is also possible to use mixtures of the solvents mentioned.

Suitable bases are, in general, inorganic compounds, such as alkali metal and alkaline earth metal hydroxides, such as LiOH, NaOH, KOH, and Ca(OH)$_2$, alkali metal and alkaline earth metal carbonates, such as Li$_2$CO$_3$, Na$_2$CO$_3$, K$_2$CO$_3$, and CaCO$_3$, and also alkali metal bicarbonates, such as NaHCO$_3$, KHCO$_3$, moreover organic bases, e.g. tertiary amines, such as trimethylamine (NMe$_3$), triethylamine (NEt$_3$), triisopropylethylamine, and N-methylpiperidine, pyridine, substituted pyridines, such as collidine, lutidine, and 4-dimethylaminopyridine, and also bicyclic amines. Particular preference is given to alkali metal bicarbonates, and carbonates, such as NaHCO$_3$ or K$_2$CO$_3$. The bases are generally employed in catalytic amounts; however, they can also be used in equimolar amounts, in excess or, if appropriate, as solvent.

The reaction step can only be performed in the presence of a hydrogenation catalyst. As used herein, the term "hydrogenation catalyst" covers heterogeneous and homogeneous hydrogenation catalysts, but preferably refers to heterogeneous catalysts. It is known in the art that platinum, palladium, rhodium, and ruthenium form highly active catalysts. Non-precious metal catalysts, such as catalysts based on nickel, such as Raney nickel and Urushibara nickel, are economical alternatives. In a preferred embodiment, the hydrogenation catalyst is selected from the group consisting of platinum or palladium on a carrier, Raney nickel, and Raney cobalt. Raney nickel is particularly preferred.

This reaction is carried out in the presence of hydrogen or a hydrogen source, preferably hydrogen is used. The reaction is in general carried out under atmospheric pressure, which usually is in the range from 0.1 to 10 bar, preferably in the range of from 0.1 to 1 bar.

The starting materials are generally reacted with one another in equimolar amounts. In terms of yield, it may be advantageous to employ an excess of III, based on II.

The nitrile of formula II is obtained by reaction of a compound of formula IV wherein R$^4$ is preferably C$_1$-C$_4$-alkyl, with a halogen compound of formula V, wherein X is a halogen atom, preferably bromo.

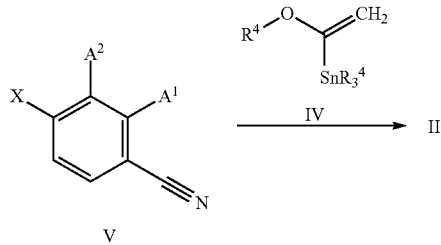

Such transformation is known as Stille reaction, it is usually carried out at temperatures of from 0° C. to 150° C., preferably from 100° C. to 120° C., in an inert solvent, in the presence of a catalyst [cf. Organic Reactions (New York) (1997), 50, 1-652].

Suitable solvents are aliphatic hydrocarbons such as pentane, hexane, cyclohexane, and petrol ether, aromatic hydrocarbons such as toluene, o-, m-, and p-xylene, halogenated hydrocarbons such as methylene chloride, chloroform, and chlorobenzene, ethers such as diethylether, diisopropylether, tert.-butylmethylether, dioxane, anisole, and THF, esters such as ethyl acetate, methyl acetate, isopropyl acetate, nitriles such as acetonitrile, and propionitrile, ketons such as acetone, methyl ethyl ketone (MEK), diethyl ketone, and tert.-butyl methyl ketone (MTBK), alcohols such as methanol, ethanol, n-propanol, isopropanol, n-butanol, and tert.-butanol, moreover dimethyl sulphoxide (DMSO), DMF, and DMA, preferably aromatic hydrocarbons such as toluene. It is also possible to use mixtures of the solvents mentioned.

Depending from the catalyst the presence of a base may be advantageous. Suitable bases are, in general, inorganic compounds, such as alkali metal and alkaline earth metal hydroxides, such as LiOH, NaOH, KOH, and Ca(OH)$_2$, alkali metal and alkaline earth metal hydrides, such as LiH, NaH, KH, and CaH$_2$, alkali metal and alkaline earth metal carbonates, such as Li$_2$CO$_3$, K$_2$CO$_3$, and CaCO$_3$, and also alkali metal bicarbonates, such as NaHCO$_3$, moreover organic bases, for example tertiary amines, such as NMe$_3$, NEt$_3$, triisopropylethylamine, and N-methylpiperidine, pyridine, substituted pyridines, such as collidine, lutidine, and 4-dimethylaminopyridine, and also bicyclic amines.

The bases are generally employed in catalytic amounts; however, they can also be used in equimolar amounts, in excess or, if appropriate, as solvent.

Cu and F salts, particularly CuI and CsF, are preferably added as catalysts [cf. Angew. Chem. Int. Ed., 2004, 43, 1132-1136].

The palladium catalysts used are generally produced in situ from at least one palladium(II) salt or a palladium(0) compound and the corresponding phosphine ligands. However, they may also be used directly as palladium(0) compound without reducing the initial catalytic activity. Suitable palladium sources are for example selected from the group consisting of palladium trifluoroacetate, palladium fluoroacetylacetonate, Pd(OAc)$_2$, Pd(OCOCH$_2$CH$_3$)$_2$, Pd(OH)$_2$, PdCl$_2$, PdBr$_2$, Pd(acac)$_2$ (acac=acetylacetonate), Pd(NO$_3$)$_2$, Pd(dba)$_2$, Pd$_2$dba$_3$ (dba=dibenzylideneacetone), Pd(CH$_3$CN)$_2$Cl$_2$, Pd(PhCN)$_2$Cl$_2$, Li[PdCl$_4$], Pd/C or palladium nanoparticles. A preferred embodiment envisages the use of methyldi(C$_{3-8}$-alkyl)phosphine or tri(C$_{3-8}$-alkyl)phosphine ligands which are branched in the alkyl part or salts thereof, particularly preferably of methyldi(tert-butyl)phosphine and tri(tert-butyl)phosphine, as ligand. The trialkylphosphine may also be used as trialkylphosphonium salt such as tetrafluoroborate (Org. Lett. 2001, 3, 4295), perchlorate or hydrogen sulphate and released therefrom in situ with a base. The molar ratio of palladium to the phosphine ligand should be between 4:I and 1:100 and is preferably between I:I and I:5, particularly preferably between I:I and I:2. According to the invention, it is also possible to use Pd[P(t-But)$_3$]$_2$ directly, the preparation of which is described in (J. Amer. Chem. Soc. 1976, 98, 5850; J. Amer. Chem. Soc. 1977, 99, 2134; J. Am. Chem. Soc. 2001, 123, 2719). A further preferred embodiment involves the use of 1,1-bis(di-t-butylphosphino)ferrocene (D. t. BPF) as ligand on the palladium. When carrying out the reaction, the catalyst system (Pd+ligand) can be added together or separately either at room temperature or at an elevated temperature. The system can be prepared separately, immediately before the reaction is carried out, by combining a Pd salt and the ligand, or it can be purchased in crystalline form. Also possible is the direct addition of the ligand and then of the palladium salt to the batch (in situ process).

Particularly preferred catalysts are selected from the following: Pd tetrakis, PdCl$_2$(PPh$_3$)$_2$, Cl$_2$Pd(dppf), Pd$_2$(dba)$_3$, Pd(OAc)$_2$, and PdCl$_2$. Particularly preferred ligands are selected from the following: PPh$_3$, dppf, 2,2'-bis-(diphenylphosphino)-1,1'-binaphthyl (BINAP), AsPh$_3$, (tBu)$_3$P, and tri(o-tolyl)phosphine(tri(o-tol)P).

The starting materials are generally reacted with one another in equimolar amounts. In terms of yield, it may be advantageous to employ an excess of II, based on III.

Alternatively the nitrile of formula II can be obtained under Heck reaction conditions by reaction of a compound of formula IVa, wherein R$^{4a}$ is C$_1$-C$_4$-alkyl, with the halogen compound of formula V,

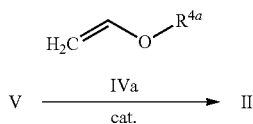

This transformation is usually carried out at temperatures of from 0° C. to 150° C., preferably from 60 to 120° C., in an inert solvent, in the presence of a base, and a catalyst [cf. Organic Reactions Wiley: Hoboken, N.J., 2002; Vol 60, Chapter 2].

Suitable solvents are aromatic hydrocarbons such as toluene, o-, m-, and p-xylene, halogenated hydrocarbons such as methylene chloride, chloroform, and chlorobenzene, ethers such as diethylether, diisopropylether, MTBE, dioxane, anisole, and THF, nitrils such as acetonitrile, and propionitrile, moreover DMSO, DMF, and DMA, preferably aromatic hydrocarbons such as toluene. It is also possible to use mixtures of the solvents mentioned.

Suitable bases are, in general, inorganic compounds, such as alkali metal and alkaline earth metal hydroxides, such as LiOH, NaOH, KOH, and Ca(OH)$_2$, alkali metal and alkaline earth metal carbonates, such as Li$_2$CO$_3$, K$_2$CO$_3$, and CaCO$_3$, and also alkali metal bicarbonates, such as NaHCO$_3$, alkali earth metal phosphates such as K$_3$PO$_4$, K$_2$HPO$_4$, KH$_2$PO$_4$, moreover organic bases, for example tertiary amines, such as NMe$_3$, NEt$_3$, triisopropylethylamine and N-methylpiperidine, pyridine, substituted pyridines, such as collidine, lutidine and 4-dimethylaminopyridine, and also bicyclic amines. Particular preference is given to Na$_2$CO$_3$, K$_2$CO$_3$, NEt$_3$. The bases are generally employed in catalytic amounts; however, they can also be used in equimolar amounts, in excess or, if appropriate, as solvent.

The catalyst used in the processes of the invention is preferably a complex compound of Pd, Pt, Ni, Rh, Ir and Ru; Pd being particularly preferred. Suitable catalysts are, in general, composed of a neutral palladium species and a phosphine ligand. The complex compound contains, apart the central transition metal, one or more ligands. Preferred ligands are mono- or bidentate ligands. More preferred complexes comprise at least one phosphorus-containing compound as ligand. The phosphorus-containing compounds are preferably selected from among PF$_3$, phosphols, phosphabenzenes, monodentate, bidentate and polydentate phosphine, phosphinite, phosphonite, phosphoramidite and phosphite ligands and mixtures thereof. More preferred are P(III)-containing compounds. Even more preferred ligands are mono- or bidentate phosphorus-containing ligands; preferably mono- or bidentate P(III)-containing ligands. In one embodiment, particularly preferred are bidentate P-containing ligands, especially bidentate P(III)-containing ligands.

In an alternative embodiment, particularly preferred are monodentate P-containing ligands, especially monodentate P(III)-containing ligands. Suitable phosphorus-containing ligands are described, e.g., in Beller, J. Molecular Catalysis, A, 104, 1995, 17-85. Preferred monodentate and bidentate phosphorus-containing ligands are those disclosed in WO2011/161130, pages 25 to 37.

Specific ligands are the following: 9,9-Dimethyl-4,5-bis (diphenylphosphino)xanthene (Xanthphos Triphenylphosphine (TPP), Triphenylphosphite (TPPit), Tri-(2-(1,1-dimethylethyl)-4-methoxy-phenyl)-phosphite (tBuOMeTPPit), racemic-2,2'-Bis(diphenylphosphino)-1,1'-binaphthyl (BINAP), Tricyclohexylphosphine (CyH$_3$P),), 1,6-Bis(diphenylphosphino)hexane (DPPH), 2,6-Bis(2,5-dimethylphenyl)-1-octyl-4-phenylphosphacyclohexan (PCH). Tri(o-tolyl)phosphine(tri(o-tol)P; [1,1'-bis(diphenylphosphino)-ferrocene] (dppf); catalyst), [1,3-bis(diphenylphosphino) propane] (dppp; ligand), Meso-2,4-bis(diphenylphophino) pentane (mBDPP; ligand) 1,4-(diphenylphophino)butane (dppb; ligand)

In a further embodiment preference is given to a bis phosphine ligand, particularly to 1,3-Bis(diphenylphosphino)propane (dppp). In a further embodiment preference is given to a bis phosphine ligand, particularly to, Meso-2,4-bis(diphenylphophino)pentane (mBDPP; ligand).

Specific catalysts are the following: Dichloro[1,3-bis(diphenylphosphino)propane] palladium(II) (Complex 130), Dichloro(1,10-phenanthroline)-palladium(II) (Complex 34), Dichloro[1,1'-bis(diphenylphosphino)-ferrocene]palladium (II), also complex with dichloromethane (Complex 128).

Specific preference is given to trans-[(2-tolyl)$_3$P]$_2$PdCl$_2$, Palladium tetrakis, Pd(dppf)C$_2$, meso-2,4-bis(diphenylphosphino)pentane, 1,4-di(phenylphosphino)-butane as catalysts.

The starting materials are generally reacted with one another in equimolar amounts. In terms of yield, it may be advantageous to employ an excess of IVa, based on V.

Alternatively, compounds of formula II can be obtained by reacting the halogen compound of formula V with a Grignard reagent Hal-Mg—R', followed by addition of an acetyl derivative of formula IVb, wherein X is a nucleophilic leaving group halogen, C$_1$-C$_6$-alkoxy, or N(CH$_3$)OCH$_3$.

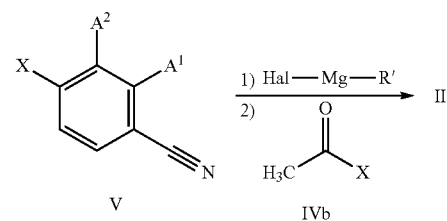

This transformation is usually carried out at temperatures of from −100° C. to 100° C., preferably from −78° C. to 25° C., in an inert solvent, in the presence of a base [cf. WO2015/91045].

Suitable solvents are aliphatic hydrocarbons such as pentane, hexane, cyclohexane, and petrol ether, aromatic hydrocarbons such as toluene, o-, m-, and p-xylene, ethers such as diethylether, diisopropylether, MTBE, dioxane, anisole, and THF, preferably ethers. It is also possible to use mixtures of the solvents mentioned.

Preferably the reaction is carried out in the presence of a Cu(I)-catalyst, such as Cu halogenides, Cu halogenide complexed with DMS, CuCN, Cu(NO)$_{1-2}$, or Cu(OTf)$_{1-2}$. The Cu-catalyst is preferably used in catalytic amounts [cf WO2013/185103].

Preferably a Grignard reagent R'—Mg-Hal is used in the process. R' in the Grignard reagent is $C_1$-$C_4$-alkyl or $C_3$-$C_6$-cycloalkyl, in particular is selected from $CH_3$, $C_2H_5$, iso-propyl, tert-butyl, sec-butyl and cyclopropyl. Specifically, R' in the Grignard reagent is selected from isopropyl, tert-butyl, sec-butyl and cyclopropyl. In one specific embodiment, R' is isopropyl. In one further embodiment, R' is sec-butyl. Hal stands for halogen, in particular Cl or Br. Also more than one Grignard reagent can be used in the same reaction, such as, for example the Grignard reagent, wherein Hal is Br together with the respective reagent (having the same R'), wherein Hal is Cl. In one embodiment Hal is Cl and R' in the Grignard reagent is selected from isopropyl, tert-butyl, sec-butyl and cyclopropyl. In a further embodiment, Hal is Br and R' in the Grignard reagent is isopropyl, tert-butyl, sec-butyl or cyclopropyl. In one preferred embodiment, the Grignard reagent is (iso-propyl)-Mg—Cl or (iso-propyl)-Mg—Br. Alternatively the Grignard reagent is (sec-butyl)-Mg—Cl or (sec-butyl)-Mg—Br.

Preferably, the Grignard reagent is used in an amount of 1 eq to 2 eq, in particular 1.1 to 1.8 eq, more specifically 1.2 to 1.6 eq, in relation to one equivalent of compound V. In particular the amounts of 1.3 to 1.5, more particularly 1.2 to 1.4 per mole of compound V may be favorable according to the present invention. Usually, the Grignard reagent is used in excess, preferably in slight excess as mentioned above.

One further embodiment relates to the inventive process, wherein Mg is used then forming a Grignard reagent with compound V and reacting with compound IVb. It can be preferred if Mg is used in an amount slightly less than compound V. Here, the same details regarding solvents apply.

As generally known to the skilled person, the structure of a Grignard reagent can be described by the so-called Schlenck equilibrium. A Grignard reagent undergoes a solvent-dependent equilibrium between different magnesium compounds. The Schlenck equilibrium for the Grignard reagent used according to the present invention can be schematically illustrated as follows:

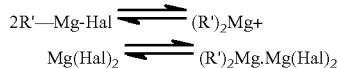

For general information regarding structures of Grignard reagents [cf. Journal of Chemical Education, Vol. 66, 7, 1999, pp 586].

According to an embodiment of the process, LiCl is added to the reaction mixture. According to an alternative, before contacting the Grignard reagent with the reagents of the process, it is brought together with LiCl, thereby forming an addition product R'MgHal.LiCl. According to this alternative, R'MgHal.LiCl is then used. The use of LiCl together with Grignard reagents is generally known in the art, see for example Angew. Chem. Int. Ed. 2004, 43, 3333 and Angew. Chem. Int. Ed. 2006, 45, 159.

The Grignard reagents or their addition products with LiCl are commercially available or can be made according to processes well-known to the skilled person [cf. Angew. Chem. Int. Ed. 2004, 43, 3333].

The reaction takes place in the presence of a transmetalating reagent. Suitable reagents are n-butyllithium, s-butyllithium, t-butyllithium, methyllithium, phenyllithium, $C_1$-$C_6$-alkyl-MgCl, $C_1$-$C_6$-alkyl-MgBr, $C_1$-$C_6$-alkyl-MgI, the magnesia compounds are preferably used in the presence of LiCl. Particular preference is given to: t-Butyllithium, i-PrMgCl, i-PrMgCl/LiCl.

The reaction may be facilitated further by transmetallation to a copper species. Suitable copper salts are: Cu halogenides, Cu halogenide complexed with DMS, CuCN, Cu(NO)$_{1-2}$, or Cu(OTf)$_{1-2}$.

The starting materials are generally reacted with one another in equimolar amounts. The Cu(I)-catalyst is present preferably in an amount of 0.005 to 0.065 mole equivalents per 1 mole of compound V.

In terms of yield, it may be advantageous to employ an excess of IVb, based on V.

The halogen compound of formula V can be obtained by Sandmeyer reaction of an aniline derivative of formula VI with a nitrosating agent in the presence of a halogen source.

This transformation is usually carried out at temperatures of from −5° C. to 115° C., preferably from 0° C. to 70° C., in an inert solvent, in some cases in the presence of an acid and a catalyst [cf. Science of Synthesis, 2007, 31, 86; Science of Synthesis, 2007, 31, 132; Science of Synthesis, 2007, 31, 260; Chem. Rev., 1947, 40 (2), 251].

Suitable nitrosating agent are sodium nitrite, potassium nitrite, alkyl nitrites, preferably tert-butyl nitrite, and 3-methylbutyl nitrite, tert-butyl thionitrite, tert-butyl thionitrate, nitrous acid, and nitrosyl complex of copper(II) chloride ($CuCl_2$—NO).

Suitable halogen sources are halogentrimethylsilane, copper(II) halogenid, copper (I) halogennide, bromodimethylsulfonium bromide (generated in situ by hydrobromic acid and DMSO), tetraalkylammonium halogenide, preferably tetra-n-butylammonium halogenide, sodium halogenide, potassium halogenide, lithium halogenide, iodine, HF, HCl, HBr, and HI.

Suitable solvents are aliphatic hydrocarbons such as pentane, hexane, cyclohexane, and petrol ether, aromatic hydrocarbons such as benzene, toluene, o-, m-, and p-xylene, halogenated hydrocarbons such as methylene chloride, chloroform, and chlorobenzene, $CCl_4$, ethers such as dioxane, and THF, nitrils such as acetonitrile, ketons such as acetone, alcohols such as methanol, ethanol, moreover DMSO, DMF, DMA, and water, preferably acetonitrile. It is also possible to use mixtures of the solvents mentioned.

A catalyst can be used. Suitable catalysts are copper, preferably as copper powder, copper salts, preferably copper (I) halogenides and copper (II) halogenides. The catalysts are generally employed in catalytic amounts; however, they can also be used in equimolar amounts, or in excess.

An acid can be used. Suitable acids and acidic catalysts are in general anorganic acids such as nitrous acid, hydrofluoric acid, hydrochloric acid, hydrobromic acid, hydrofluoric acid, and sulphuric acid, moreover organic acids such as acetic acid, camphor sulphonic acid, and trifluoro acetic acid.

The acids are generally employed in catalytic amounts; however, they can also be used in equimolar amounts, in excess or, if appropriate, as solvent.

The process is generally done as one-pot reaction. The reaction can be done as well stepwise. First, a diazonium salt is formed by reacting the aniline derivative of formula VI with a nitrosating agent. In a second step, the diazonium salt is reacting with a halogen source.

The aniline derivative VI can be obtained by reductive dehalogenation from the chloro compound VII with hydrogen or a hydrogen source in the presence of a hydrogenation catalyst.

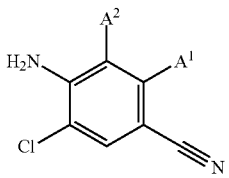

VII

This transformation is usually carried out at temperatures of from 0° C. to 100° C., preferably from 20° C. to 80° C., in an inert solvent, in the presence of a catalyst.

For this transformation, hydrogen or a hydrogen source can be used. A preferred hydrogen source is potassium formate. This particular reaction will be carried out under atmospheric pressure. In a preferred embodiment, hydrogen is used. The preferred hydrogen pressure in the range from 0.1 to 10 bar, preferably in the range of from 0.1 to 1 bar.

The reaction step can only be performed in the presence of a hydrogenation catalyst. As used herein, the term "hydrogenation catalyst" covers heterogeneous and homogeneous hydrogenation catalysts, but preferably refers to heterogeneous catalysts. It is known in the art that platinum, palladium, rhodium, and ruthenium form highly active catalysts. Non-precious metal catalysts, such as catalysts based on nickel (such as Raney nickel and Urushibara nickel) are economical alternatives. Preferred hydrogenation catalysts include platinum, palladium, rhodium, ruthenium, nickel, or cobalt on carriers such as carbon. In a preferred embodiment, the hydrogenation catalyst is selected from the group consisting of platinum or palladium on a carrier, Raney nickel, and Raney cobalt, and is preferably platinum or palladium on carbon.

Optionally, the catalyst may be doped with sulfur or selenium. This can enhance the selectivity of the catalyst.

In a particularly preferred embodiment, the hydrogenation catalyst is palladium or platinum on carbon, wherein the palladium or platinum content is preferably in the range of from 0.1 to 15% by weight, more preferably from 0.5 to 10% by weight based on the carrier material.

In another particularly preferred embodiment, the amount of palladium or platinum used is from 0.001 to 1% by weight, preferably from 0.01 to 0.1% by weight based on the starting material.

Suitable solvents include water and aliphatic hydrocarbons such as pentane, hexane, cyclohexane and petroleum ether; aromatic hydrocarbons such as toluene, o-, m- and p-xylene; halogenated hydrocarbons such as methylene chloride, chloroform and chlorobenzene; alcohols such as methanol, ethanol, n-propanol, isopropanol, n-butanol and tert-butanol; $C_2$-$C_4$-alkandiols, such as ethylene glycol or propylene glycol; ether alkanols such as diethylene glycol; carboxylic esters such as ethyl acetate; N-methylpyrrolidone; dimethylformamide; and ethers including open-chained and cyclic ethers, especially diethyl ether, MTBE, 2-methoxy-2-methylbutane, cyclopentylmethylether, 1,4-dioxane, THF, and 2-methyltetrahydrofuran, in particular THF, MTBE, and 2-methyltetrahydrofuran. Mixtures of said solvents can also be used. Preferred solvents are protic solvents, preferably alcohols selected from the group consisting of such as methanol, ethanol, n-propanol, isopropanol, n-butanol and tert-butanol.

As a side product of the reaction step, hydrogen chloride is produced. A HCl scavenger can be present in the reaction mixture or added only after removal of the hydrogenation catalyst. Preferably, the HCl scavenger is present in the reaction mixture.

As used herein, the term "HCl scavenger" refers to a chemical substance, which is added to a reaction mixture in order to remove or de-activate hydrogen chloride (HCl). Preferred HCl scavengers include bases, buffers, and precursors of ionic liquids, which are defined in further detail below. Of particular interest is the capability of HCl scavengers to bind protons. Preferred HCl scavengers are provided below.

Bases include alkali metal and alkaline earth metal hydroxides, alkali metal and alkaline earth metal oxides, alkali metal and alkaline earth metal hydrides, alkali metal amides, alkali metal and alkaline earth metal carbonates, alkali metal bicarbonates, alkali metal alkyls, alkylmagnesium halides, alkali metal and alkaline earth metal alcoholates, tertiary amines, pyridines, bicyclic amines, ammonia, and combinations thereof.

Buffers include aqueous and non-aqueous buffers, and are preferably non-aqueous buffers. Preferred buffers include buffers based on acetate or formate, e.g. sodium acetate or ammonium formate. Precursors of ionic liquids include imidazoles.

In one preferred embodiment, the HCl scavenger comprises at least one base.

In one particularly preferred embodiment, the base is selected from alkali metal and alkaline earth metal hydroxides, in particular from the group consisting of LiOH, NaOH, KOH, and Ca(OH)$_2$.

In another particularly preferred embodiment, the base is selected from alkali metal and alkaline earth metal oxides, in particular from the group consisting of Li$_2$O, Na$_2$O, CaO, and MgO.

In another particularly preferred embodiment, the base is selected from alkali metal and alkaline earth metal hydrides, in particular from the group consisting of LiH, NaH, KH, and CaH$_2$.

In another particularly preferred embodiment, the base is selected from alkali metal amides, in particular from the group consisting of LiNH$_2$, NaNH$_2$, and KNH$_2$.

In another particularly preferred embodiment, the base is selected from alkali metal and alkaline earth metal carbonates, in particular from the group consisting Li$_2$CO$_3$K$_2$CO$_3$, and CaCO$_3$.

In another particularly preferred embodiment, the base is selected from alkali metal bicarbonates, and is preferably NaHCO$_3$, and KHCO$_3$.

In another particularly preferred embodiment, the base is selected from alkali metal alkyls, in particular from the group consisting of methyllithium, butyllithium, and phenyllithium.

In another particularly preferred embodiment, the base is selected from alkylmagnesium halides, and is preferably methylmagnesiumchloride.

In another particularly preferred embodiment, the base is selected from alkali metal and alkaline earth metal alcoholates, in particular from the group consisting of sodium methanolate, sodium ethanolate, potassium ethanolate, potassium tert-butanolate, and dimethoxymagnesium.

In another particularly preferred embodiment, the base is a tertiary amine, in particular NMe$_3$, NEt$_3$, diisopropylethylamine, or N-methylpiperidine.

In another particularly preferred embodiment, the base is a pyridine including substituted pyridines such as collidine, lutidine, and 4-dimethylaminopyridine.

In another particularly preferred embodiment, the base is a bicyclic amine.

In another particularly preferred embodiment, the base is ammonia.

In a most preferred embodiment the HCl scavenger is KOH or any one of the above defined carbonates.

The bases may be used in equimolar quantities, in excess or, where appropriate, as solvents.

In another preferred embodiment, the HCl scavenger comprises at least one buffer.

In a particularly preferred embodiment, the buffer is anhydrous sodium acetate or anhydrous ammonium formate.

In another preferred embodiment, the HCl scavenger comprises a precursor of an ionic liquid.

In a particularly preferred embodiment, the precursor of the ionic liquid is an imidazole compound, which forms an ionic liquid after having reacted with the HCl, which is set free in the hydrogenation/dehalogenation reaction. A nonpolar organic phase comprising the desired dechlorinated compound can then be easily separated from the newly formed ionic liquid.

The chloro nitrile compound VII can be obtained from the amide of formula VIII

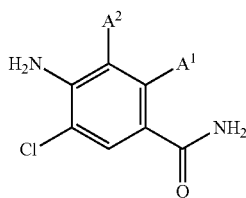

VIII

This transformation is usually carried out at temperatures of from −78° C. to 150° C., preferably from −5° C. to 65° C., in an inert solvent, in the presence of a dehydrating reagent or reagent combination [cf. Science of Synthesis 2004, 19, 121].

Suitable dehydrating reagents or reagent combinations are LiAlH$_4$, P$_2$O$_5$, SOCl$_2$, POCl$_3$, acetic anhydride, trifluoroacetic anhydride, trifluoroacetic chloride, 4-toluenesulfonyl chloride, 2,4,6-trichloro-1,3,5-triazine (cyanuric chloride), trichloroacetyl chloride, triphenylphosphine/CCl$_4$, Burgess reagent, oxalyl chloride/DMSO, trifluoromethanesulfonic anhydride, methylsulfonyl chloride, silylmethanesulfonyl phosphate, N-[3-(dimethylamino)propyl]-N-ethylcarbodiimide, 2,2,2-trichloroethylchloroformate, trichloromethyl chloroformate, PCl$_5$, benzene sulfonyl chloride, preferably POCl$_3$, and SOCl$_2$.

Suitable solvents are aliphatic hydrocarbons, aromatic hydrocarbons, halogenated hydrocarbons such as methylene chloride, ethers such as dioxane, nitrils such as acetonitrile, moreover DMSO, DMF, and DMA. It is also possible to use mixtures of the solvents mentioned or, preferably, run the reaction in POCl$_3$ without solvent.

If appropriate, it is also possible to add a base to the dehydrating reagent or reagent combination. Suitable bases are, in general, organic bases, for example tertiary amines, such as NMe$_3$, NEt$_3$, diisopropylethylamine and N-methylpiperidine, pyridine, substituted pyridines, such as collidine, lutidine and 4-dimethylaminopyridine, and also bicyclic amines. Particular preference is given to NMe$_3$ and pyridine. The bases are generally employed in equimolar amounts; however, they can also be used in catalytic amounts, in excess or, if appropriate, as solvent.

The amide of formula VIII is obtained from the corresponding benzoic acid of formula IX by standard amidation processes, which are known in the art.

This transformation is usually carried out at temperatures of from −50° C. to 150° C., preferably from 0° C. to 90° C., in an inert solvent, in the presence of ammonia and a base, an acid, and optionally a catalyst [cf. Houben-Weyl, Methods of Organic Chemistry, Vol. E5, pp. 941-1045, Georg-Thieme Verlag, Stuttgart and N.Y. 1985]

Suitable solvents are aliphatic hydrocarbons, aromatic hydrocarbons such as toluene, o-, m-, and p-xylene, halogenated hydrocarbons, ethers such as diethylether, diisopropylether, tert.-butylmethylether (MTBE), dioxane, anisole, and THF, nitrils such as acetonitrile, and propionitrile, ketons, alcohols, moreover DMSO, DMF, and DMA, preferably DMF, toluene, THF, MTBE, or acetonitrile. It is also possible to use mixtures of the solvents mentioned. Suitable bases are, in general, inorganic compounds, such as alkali metal and alkaline earth metal hydroxides, alkali metal and alkaline earth metal oxides, alkali metal and alkaline earth metal carbonates, and also alkali metal bicarbonates, moreover, organic bases, for example tertiary amines, such as NMe$_3$, NEt$_3$, diisopropylethylamine and N-methylpiperidine, pyridine, substituted pyridines, such as collidine, lutidine and 4-dimethylaminopyridine, and also bicyclic amines. Particular preference is given to imidazole, and NEt$_3$. The bases are generally employed in catalytic amounts; however, they can also be used in equimolar amounts, in excess or, if appropriate, as solvent. Suitable acids and acidic catalysts are in general anorganic acids such as hydrofluoric acid, hydrochloric acid, hydrobromic acid, sulphuric acid und perchloric acid, moreover, organic acids such as formic acid, acetic acid, propionic acid, oxalic acid, toluene sulphonic acid, benzene sulphonic acid, camphor sulphonic acid, citric acid, and trifluoro acetic acid. A peptide coupling reagent can be used. A suitable list of reagents can be found in WO 2011003793, pp. 53-54.

Alternatively, the acid is first converted to an acid chloride through reaction with SOCl$_2$ or POCl$_3$, optionally in an organic solvent, then further reacted with at least 1 equiv. ammonia, optionally in the presence of a base and optionally in the presence of a catalyst and solvent to form the amide. The reaction conditions are known for the skilled artisan.

Compounds of formula I are valuable intermediates for the preparation of active compounds of formula XII via an intermediate of formula XI.

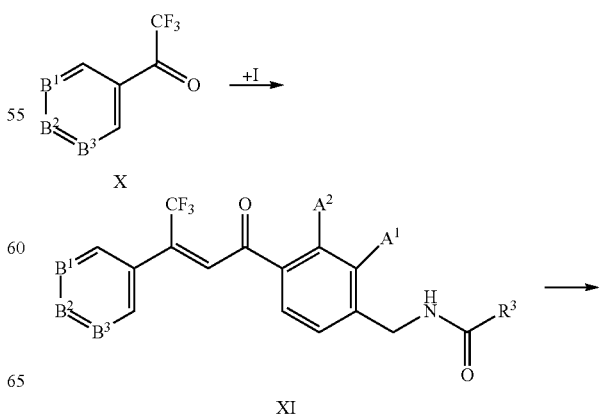

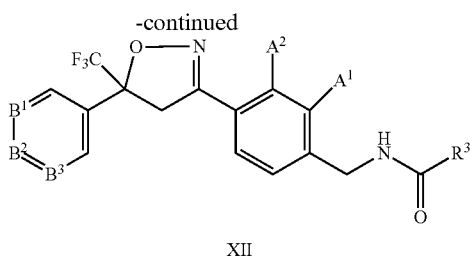

XII

The compounds of formula XI are preferably obtained by condensation of a ketone of formula X with the acetyl compound of formula I.

This transformation is usually carried out at temperatures of from 0° C. to +150° C., preferably from 20° C. to +120° C., in an inert solvent, in the presence of a base [cf. WO 2013/092943]

Suitable solvents are aliphatic hydrocarbons such as pentane, hexane, cyclohexane, and petrol ether, aromatic hydrocarbons such as toluene, o-, m-, and p-xylene, halogenated hydrocarbons such as $CH_2Cl_2$, $CHCl_3$, dichloroethane (DCE), chlorobenzene, and trifluorobenzene, ethers such as diethyl ether, diisopropylether, MTBE, 1,4-dioxane, anisole, and THF, nitrils such as acetonitrile, and propionitrile, alcohols such as methanol (MeOH), ethanol, n-propanol, isopropanol, n-butanol, and tert.-butanol, preferably aliphatic hydrocarbons or halogenated hydrocarbons such as DCE. It is also possible to use mixtures of the solvents mentioned.

Suitable bases are, in general, inorganic compounds, such as alkali metal and alkaline earth metal hydroxides, such as LiOH, NaOH, KOH and $Ca(OH)_2$, alkali metal and alkaline earth metal oxides, such as $Li_2O$, $Na_2O$, CaO, and MgO, alkali metal and alkaline earth metal carbonates, such as $Li_2CO_3$, $K_2CO_3$, $Na_2CO_3$, $CaCO_3$, and $Cs_2CO_3$ and also alkali metal bicarbonates, such as $NaHCO_3$, moreover organic bases, for example tertiary amines, such as $N(CH_3)_3$, $N(C_2H_5)_3$, diisopropylethylamine and N-methylpiperidine, pyridine, substituted pyridines, such as collidine, lutidine and 4-dimethylaminopyridine, and also bicyclic amines. Particular preference is given to alkali metal and alkaline earth metal carbonates and organic bases, especially sodium, potassium or cesium carbonate and $NEt_3$. The bases are generally employed in catalytic amounts; however, they can also be used in equimolar amounts, in excess or, if appropriate, as solvent. It is also possible to use mixtures of the bases mentioned.

The cyclysation of the α,β-unsaturated ketone of formula XI to an isoxazoline active compound of formula XII can be achieved in a reaction with hydroxylamine. Suitable reaction conditions are described, e.g., in WO 2012/158396. Suitably, hydroxylamine is used as the hydrochloride salt. The reaction is generally carried out in the presence of a base, such as NaOH, KOH, $Na_2CO_3$ and the like. Suitable solvents are aqueous, such as water or mixtures of water with polar solvents, such as tetrahydrofuran, dioxane and lower alkanols.

The reaction mixtures are worked up in a customary manner, for example by mixing with water, separating the phases and, if appropriate, chromatographic purification of the crude products. Some of the intermediates and end products are obtained in the form of colorless or slightly brownish viscous oils which are purified or freed from volatile components under reduced pressure and at moderately elevated temperature. If the intermediates and end products are obtained as solids, purification can also be carried out by recrystallization or digestion.

If individual compounds cannot be prepared via the above-described routes, they can be prepared by derivatization of other compounds I or by customary modifications of the synthesis routes described. For example, in individual cases, certain compounds I can advantageously be prepared from other compounds I by ester hydrolysis, amidation, esterification, ether cleavage, olefination, reduction, oxidation, and the like.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration.

The term "compound(s) according to the invention", or "compounds of formula I" comprises the compound(s) as defined herein as well as a stereoisomer, salt, tautomer or N-oxide thereof. The term "compound(s) of the invention" is to be understood as equivalent to the term "compound(s) according to the invention", therefore also comprising a stereoisomer, salt, tautomer or N-oxide thereof.

The radicals attached to the backbone of formula I may contain one or more centers of chirality. In this case the formula I are present in the form of different enantiomers or diastereomers, depending on the substituents. The present invention relates to every possible stereoisomer of the formula I, i.e. to single enantiomers or diastereomers, as well as to mixtures thereof.

The compounds of formula I may be amorphous or may exist in one or more different crystalline states (polymorphs) which may have different macroscopic properties such as stability or show different biological properties such as activities. The present invention relates to amorphous and crystalline compounds of formula I, mixtures of different crystalline states of the respective compound I, as well as amorphous or crystalline salts thereof.

The organic moieties mentioned in the above definitions of the variables are—like the term halogen—collective terms for individual listings of the individual group members. The prefix $C_nC_m$ indicates in each case the possible number of carbon atoms in the group.

The term "halogen" denotes in each case fluorine, bromine, chlorine or iodine, in particular fluorine, chlorine or bromine.

The term "alkyl" as used herein and in the alkyl moieties of alkoxy, alkylcarbonyl, alkylthio, alkylsulfinyl, alkylsulfonyl and alkoxyalkyl denotes in each case a straight-chain or branched alkyl group having usually from 1 to 6 carbon atoms, preferably 1 to 4 carbon atoms and in particular from 1 to 3 carbon atoms. Examples of an alkyl group are methyl, ethyl, n-propyl, isopropyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl.

The term "haloalkyl" as used herein and in the haloalkyl moieties of haloalkoxy, haloalkylthio, haloalkylcarbonyl, haloalkylsulfonyl and haloalkylsulfinyl, denotes in each case a straight-chain or branched alkyl group having usually from 1 to 6 carbon atoms, frequently from 1 to 4 carbon atoms, wherein the hydrogen atoms of this group are partially or totally replaced with halogen atoms. Preferred haloalkyl moieties are selected from $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "alkoxy" as used herein denotes in each case a straight-chain or branched alkyl group which is bound via an oxygen atom and has usually from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert.-butyloxy, and the like.

The term "cycloalkyl" as used herein and in the cycloalkyl moieties of cycloalkoxy and cycloalkylmethyl denotes in each case a monocyclic cycloaliphatic radical having usually from 3 to 6 carbon atoms, such as cyclopropyl, cyclobutyl, cyclopentyl, and cyclohexyl.

The term "alkenyl" as used herein denotes in each case a singly unsaturated hydrocarbon radical having usually 2 to 6, preferably 2 to 4 carbon atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "alkynyl" as used herein denotes in each case a singly unsaturated hydrocarbon radical having usually 2 to 6, preferably 2 to 4 carbon atoms, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "alkoxyalkyl" as used herein refers to alkyl usually comprising 1 to 2 carbon atoms, wherein 1 carbon atom carries an alkoxy radical usually comprising 1 or 2 carbon atoms as defined above. Examples are $CH_2OCH_3$, $CH_2$—$OC_2H_5$, 2-(methoxy)ethyl, and 2-(ethoxy)ethyl.

The term "heterocyclyl" includes in general 5-, or 6-membered, in particular 6-membered monocyclic heterocyclic non-aromatic radicals. The heterocyclic non-aromatic radicals usually comprise 1, 2, or 3 heteroatoms selected from N, O and S as ring members, where S-atoms as ring members may be present as S, SO or $SO_2$.

The term "4-, 5-, or 6-membered saturated, partially or fully unsaturated heterocyclic ring (HET) comprising 1, 2 or 3 heteroatoms N, O, and/or S as ring members" denotes a 4-, 5-, or 6-membered saturated, partially unsaturated or fully unsaturated heteromonocyclic ring containing 1, 2 or 3 heteroatoms which are selected from N, O, and S as ring members. Unsaturated rings contain at least one C—C and/or C—N and/or N—N double bond(s). Fully unsaturated rings contain as many conjugated C—C and/or C—N and/or N—N double bonds as allowed by the ring size. Fully unsaturated include aromatic heterocyclic rings. The heterocyclic ring may be attached to the remainder of the molecule via a carbon ring member or via a nitrogen ring member. Of course, the heterocyclic ring contains at least one carbon ring atom. If the ring contains more than one O ring atom, these are not adjacent. N and S ring atoms may be oxidized, if not mentioned otherwise. The oxidized ring atoms constitute an N-oxide, Sulfoxide (SO), and a sulfone ($SO_2$), resp., wherein the only the N- or S atom is a ring member.

Examples of a 3-, 4-, 5-, or 6-membered saturated, partially or fully unsaturated heteromonocyclic ring include: Oxiranyl, thiiranyl, aziridinyl, oxetanyl, thietanyl, azetidinyl, tetrahydrofuran-2-yl, tetrahydrofuran-3-yl, tetrahydrothien-2-yl, tetrahydrothien-3-yl, pyrrolidin-1-yl, pyrrolidin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2-tetrahydropyranyl, 4-tetrahydropyranyl, 1,3-dioxan-5-yl, 1,4-dioxan-2-yl, piperidin-1-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl and 1,2,4-hexahydrotriazin-3-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like. Examples of an 8-membered saturated heterocyclic ring include: oxocanyl, azocanyl, 1,2-, 1,3-, 1,4- and 1,5-diazocanyl and the like.

Examples of a 4-, 5-, or 6-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H] azepin-1-, -2-, -3-, -4-, -5-, -6- or -7-yl, 3,4,5,6-tetrahydro [2H]azepin-2-, -3-, -4-, -5-, -6- or -7-yl, 2,3,4,7-tetrahydro [1H]azepin-1-, -2-, -3-, -4-, -5-, -6- or -7-yl, 2,3,6,7- tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl. Examples of an 8-membered partially unsaturated heterocyclic ring include: dihydroazocinyl, tetrahydrazocinyl, hexahydroazocinyl and the like.

Examples for a 4-, 5-, or 6-membered fully unsaturated (including aromatic) heterocyclic ring are 5- or 6-membered heteroaromatic rings, such as 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 1,2,4-triazol-1-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl and 2-pyrazinyl, and also homoaromatic radicals, such as 1H-azepine, 1H-[1,3]-diazepine and 1H-[1,4]-diazepine. Examples of an 8-membered fully unsaturated saturated heterocyclic ring include: azocinyl, 1,2-, 1,3-, 1,4- and 1,5-diazocinyl and the like.

A group of preferred heterocycles HET is the following: 2-pyridyl (E-1), 3-pyridyl (E-2), 4-pyridyl (E-3), 3-pyridazinyl (E-4), 4-pyrimidinyl (E-5), 2-pyrazinyl (E-6), 2-pyrimidinyl (E-7), thiophen-2-yl (E-8), thiophen-3-yl (E-9), furan-2-yl (E-10), and furan-3-yl (E-11); heterocycles E-1, E-2, and E-7 are particularly preferred, which rings E-1 to E-11 are unsubstituted or substituted by up to 3 same or different substituents.

Another particularly preferred heterocycle is 1,2,4-triazol-1-yl.

Preferred 4-, 5-, or 6-membered saturated, partially or fully unsaturated heterocyclic rings (HET) comprising 1, 2 or 3 heteroatoms N, O, and/or S as ring members are in any positions of formula I, the following: azetidin-3-yl (H-1), dioxin-6-yl (H-2), 1,3-dioxolan-2-yl (H-3), 1,1-dioxotetrahydrothiophen-3-yl (H-4), 1,1-dioxothietan-2-yl (H-5), 1,1-dioxothietan-3-yl (H-6), imidazol-2-yl (H-7), imidazol-4-yl (H-8), imidazol-5-yl (H-9), isothiazol-3-yl (H-10), isothiazol-4-yl (H-11), isothiazol-5-yl (H-12), isoxazol-3-yl (H-13), isoxazol-4-yl (H-14), isoxazol-5-yl (H-15), isoxazoledin-4-yl (H-16), oxazol-2-yl (H-17), oxazol-4-yl (H-18), oxazol-5-yl (H-19), oxethan-3-yl (H-20), 3-oxoisoxazolidin-4-yl (H-21), 2-oxopyrrolidin-3-yl (H-22), 2-oxotetrahydrofuran-3-yl (H-23), [1,3,4]-thiadiazol-2-yl (H-24), [1,2,3]-thiadiazol-4-yl (H-25), [1,2,3]-thiadiazol-5-yl (H-26), thiazol-2-yl (H-27), thiazol-4-yl (H-28), thiazol-5-yl (H-29), thien-2-yl (H-30), thien-3-yl (H-31), thietan-2-yl (H-32), thietan-3-yl (H-33), 1-oxothietan-2-yl (H-34), 1-oxothietan-3-yl (H-35), 1-oxotetrahydrothiophen-3-yl (H-36), tetrahydrofuran-2-yl (H-37), tetrahydrofuran-3-yl (H-38), tetrahydrothiophen-3-yl (H-39), pyrazin-2-yl (E-6), pyrazol-3-yl (H-40), 2-pyridyl (E-1), 3-pyridyl (E-2), 4-pyridyl (E-3), pyridazin-3-yl (E-4), pyridazin-4-yl (H-41), 2-pyrimidinyl (E-7), 4-pyrimidinyl (E-5), 5-pyrimidinyl (H-42), and pyrrolidin-3-yl (H-43). More preferred rings HET are the following: E-1, E-7 and H-6, H-21, H-33 and H-35. Rings E-2 and E-7 are particularly preferred.

A group which is substituted with more than one substituent can be substituted by identical or different substituents if not otherwise mentioned.

With respect to the variables, the particularly preferred embodiments of the intermediates and the final products of formula XII correspond to those of the groups of the formula I.

In a particular embodiment, the variables of the compounds of the formula I have the following meanings, these meanings, both on their own and in combination with one another, being particular embodiments of the compounds of the formula I: In one preferred embodiment of the compounds of formulae I and XII, $A^1$ and $A^2$ together form a chain \$-$CH_2CH_2O$-#. Such formula I compounds correspond to the formula IA.

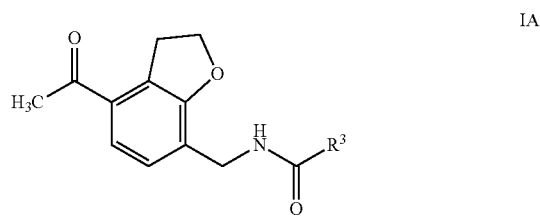

IA

In another embodiment of the invention $A^1$ and $A^2$ together form a chain —$(CH_2)_m$—, preferably —$CH_2CH_2CH_2$—.

In another embodiment $A^1$ is halogen, $CH_3$, $CF_3$, $OCHF_2$, or $C_1$-$C_4$-alkoxy, and $A^2$ is H.

Particular preference is given to the compounds of the formula I compiled in the tables below, which compounds correspond to the formula IA. Each of the groups mentioned for a substituent in the table is furthermore per se, independently of the combination in which it is mentioned, a particularly preferred aspect of the substituent in question.

In compounds of formula XII all groups $B^1$, $B^2$, and $B^3$, resp., are preferably C—$R^2$, wherein the $R^2$ groups are identical or different from each other. Accordingly preferred formula XII compounds corresponds to formula XIIA:

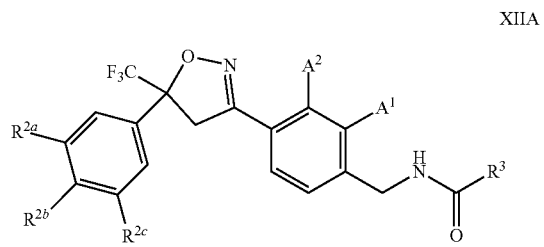

XIIA

In one embodiment, $R^{2a}$ is halogen, halomethyl, or halomethoxy, and $R^{2b}$ and $R^{2c}$ are H, or as defined for $R^{2a}$.

In another embodiment, $R^{2a}$ is F, Cl, Br, $CF_3$, or $OCF_3$, and $R^{2b}$ and $R^{2c}$ are H, or as defined for $R^{2a}$.

Preferably the combination of $R^{2a}$, $R^{2b}$, and $R^{2c}$ correspond to a line A-1 to A-31 of Table A.

TABLE A

| No. | $R^{2a}$ | $R^{2b}$ | $R^{2c}$ |
|-----|----------|----------|----------|
| A-1 | F | H | F |
| A-2 | F | F | F |
| A-3 | F | Cl | F |
| A-4 | F | Br | F |
| A-5 | F | H | Cl |

TABLE A-continued

| No. | $R^{2a}$ | $R^{2b}$ | $R^{2c}$ |
|---|---|---|---|
| A-6 | F | H | Br |
| A-7 | Cl | H | Cl |
| A-8 | Cl | Cl | Cl |
| A-9 | Cl | F | Cl |
| A-10 | Cl | Br | Cl |
| A-11 | Cl | H | Br |
| A-12 | Br | H | Br |
| A-13 | Br | F | Br |
| A-14 | Br | Cl | Br |
| A-15 | $CF_3$ | H | F |
| A-16 | $CF_3$ | H | Cl |
| A-17 | $CF_3$ | H | Br |
| A-18 | $CF_3$ | H | $CF_3$ |
| A-19 | $CF_3$ | F | F |
| A-20 | $CF_3$ | Cl | Cl |
| A-21 | $CF_3$ | Br | Br |
| A-22 | $OCF_3$ | H | F |
| A-23 | $OCF_3$ | H | Cl |
| A-24 | $OCF_3$ | H | Br |
| A-25 | $OCF_3$ | H | $CF_3$ |
| A-26 | $OCF_3$ | H | H |
| A-27 | $CF_3$ | H | H |
| A-28 | Br | H | H |
| A-29 | Cl | H | H |
| A-30 | F | H | H |
| A-31 | Cl | F | H |

Compounds of formula IA, wherein $R^3$ is selected from $C_1$-$C_6$-alkyl, $C_1$-$C_6$-haloalkyl, $C_1$-$C_4$-alkyl substituted with one radical $R^{31}$, $C_3$-$C_6$-cycloalkyl which is unsubstituted or substituted with a CN, $C_3$-$C_6$-halocycloalkyl, phenyl; and a heterocycle HET selected from E-1 to E-11 and H-1 to H-40 which rings are unsubstituted, or partially or fully substituted by same or different $R^{32}$, are particularly preferred embodiments of the invention.

Preferred $R^{32}$ groups are halogen, CN, $C_1$-$C_4$-alkyl, $C_1$-$C_4$-haloalkyl, $C_1$-$C_4$-alkoxy, and $C_1$-$C_4$-haloalkoxy.

In another embodiment $R^3$ is $C_1$-$C_4$-alkoxy, particularly tert.-butoxy.

Further preferred embodiments are listed in Table C.

TABLE C

| No. | $R^3$ |
|---|---|
| C-1 | H |
| C-2 | $CH_3$ |
| C-3 | $C_2H_5$ |
| C-4 | $CH_2CH_2CH_3$ |
| C-5 | $CH(CH_3)_2$ |
| C-6 | $CH_2CH_2CH_2CH_3$ |
| C-7 | $CH(CH_3)CH_2CH_3$ |
| C-8 | $CH_2CH(CH_3)_2$ |
| C-9 | $C(CH_3)_3$ |
| C-10 | $CH_2C(CH_3)_3$ |
| C-11 | $CH_2F$ |
| C-12 | $CHF_2$ |
| C-13 | $CF_3$ |
| C-14 | $CH_2CHF_2$ |
| C-15 | $CH_2CF_3$ |
| C-16 | $CF_2CF_3$ |
| C-17 | $CH_2CH_2CF_3$ |
| C-18 | $CH(CH_3)CF_3$ |
| C-19 | $CH(CF_3)_2$ |
| C-20 | $CF(CF_3)_2$ |
| C-21 | $CH_2CN$ |
| C-22 | $CH=CH_2$ |
| C-23 | $CH_2CH=CH_2$ |
| C-24 | $C\equiv CH$ |
| C-25 | $CH_2C\equiv CH$ |
| C-26 | CN |
| C-27 | CH=CHF |
| C-28 | $CH=CF_2$ |
| C-29 | $CF=CF_2$ |
| C-30 | c-$C_3H_5$ |
| C-31 | 1-F-c-$C_3H_4$ |
| C-32 | 1-CN-c-$C_3H_4$ |
| C-33 | c-$C_4H_7$ |
| C-34 | 1-F-c-$C_4H_6$ |
| C-35 | 1-CN-c-$C_4H_6$ |
| C-36 | cyclobut-1-enyl |
| C-37 | $CH_2$-c-$C_3H_5$ |
| C-38 | $CH_2$-(1-CN-c-$C_3H_4$) |
| C-39 | $CH_2$-c-$C_4H_7$ |
| C-40 | $CH_2$-(1-CN-c-$C_4H_6$) |
| C-41 | oxetan-2-yl |
| C-42 | oxetan-3-yl |
| C-43 | tetrahydrofuran-2-yl |
| C-44 | tetrahydrofuran-3-yl |
| C-45 | thietan-3-yl |
| C-46 | 1-oxo-thietan-3-yl |
| C-47 | 1,1-dioxo-thietan-3-yl |
| C-48 | $C_6H_5$ |
| C-49 | 2-F—$C_6H_4$ |
| C-50 | 3-F—$C_6H_4$ |
| C-51 | 4-F—$C_6H_4$ |
| C-52 | 2,3-$F_2$—$C_6H_3$ |
| C-53 | 2,4-$F_2$—$C_6H_3$ |
| C-54 | 2,5-$F_2$—$C_6H_3$ |
| C-55 | 2,6-$F_2$—$C_6H_3$ |
| C-56 | 3,4-$F_2$—$C_6H_3$ |
| C-57 | 3,5-$F_2$—$C_6H_3$ |
| C-58 | 2-Cl—$C_6H_4$ |
| C-59 | 3-Cl—$C_6H_4$ |
| C-60 | 4-Cl—$C_6H_4$ |
| C-61 | 2-$OCH_3$—$C_6H_4$ |
| C-62 | 3-$OCH_3$—$C_6H_4$ |
| C-63 | 4-$OCH_3$—$C_6H_4$ |
| C-64 | pyridin-2-yl |
| C-65 | pyridin-3-yl |
| C-66 | pyridin-4-yl |
| C-67 | 4-Cl-pyridin-3-yl |
| C-68 | pyrimidin-2-yl |
| C-69 | $CH_2OCH_3$ |
| C-70 | $CH_2OCH_2CH_3$ |
| C-71 | $CH_2OCF_3$ |
| C-72 | $CH_2SCH_3$ |
| C-73 | $CH_2SCH_2CH_3$ |
| C-74 | $CH_2SCF_3$ |
| C-75 | $CH_2S(O)CH_3$ |
| C-76 | $CH_2S(O)CH_2CH_3$ |
| C-77 | $CH_2S(O)CF_3$ |
| C-78 | $CH_2SO_2CH_3$ |
| C-79 | $CH_2SO_2CH_2CH_3$ |
| C-80 | $CH_2SO_2CF_3$ |
| C-81 | $CH(CH_3)SO_2CH_3$ |
| C-82 | $C(CH_3)_2SO_2CH_3$ |
| C-83 | $CH_2N(CH_3)_2$ |
| C-84 | $CH_2CH_2N(CH_3)_2$ |
| C-85 | $NHCH_3$ |
| C-86 | $NHCH_2CH_3$ |
| C-87 | $NHCH_2CHF_2$ |
| C-88 | $NHCH_2CF_3$ |
| C-89 | $NHCH_2CH=CH_2$ |
| C-90 | $NHCH_2C\equiv CH$ |
| C-91 | $NHCH_2CN$ |
| C-92 | NH-c-$C_3H_5$ |
| C-93 | NH-(1-CN-c-$C_3H_4$) |
| C-94 | $NHCH_2$-c-$C_3H_5$ |
| C-95 | $NHCH_2$-(1-CN-c-$C_3H_4$) |
| C-96 | $C(O)NHCH_3$ |
| C-97 | $C(O)NHCH_2CH_3$ |
| C-98 | $C(O)NHCH_2CHF_2$ |
| C-99 | $C(O)NHCH_2CF_3$ |
| C-100 | $C(O)NHCH_2CH=CH_2$ |
| C-101 | $C(O)NHCH_2C\equiv CH$ |
| C-102 | $C(O)NHCH_2CN$ |
| C-103 | $C(O)NH$-c-$C_3H_5$ |
| C-104 | $C(O)NH$-(1-CN-c-$C_3H_4$) |
| C-105 | $CH_2C(O)NHCH_3$ |
| C-106 | $CH_2C(O)NHCH_2CHF_2$ |

TABLE C-continued

| No. | R³ |
|---|---|
| C-107 | CH₂C(O)NHCH₂CF₃ |
| C-108 | CH₂C(O)NHCH₂CH=CH₂ |
| C-109 | CH₂C(O)NHCH₂C≡CH |
| C-110 | CH₂C(O)NHCH₂CN |
| C-111 | CH₂C(O)NH-c-C₃H₅ |
| C-112 | CH₂C(O)NH-(1-CN-c-C₃H₄) |
| C-113 | CH₂C(O)NHCH₂-c-C₃H₅ |
| C-114 | CH₂C(O)NHCH₂(1-CN-c-C₃H₄) |
| C-115 | NHC(O)NHCH₃ |
| C-116 | NHC(O)NHCH₂CH₃ |
| C-117 | NHC(O)NHCH₂CHF₂ |
| C-118 | NHC(O)NHCH₂CF₃ |
| C-119 | NHC(O)NHCH₂CH=CH₂ |
| C-120 | NHC(O)NHCH₂C≡CH |
| C-121 | NHC(O)NHCH₂CN |
| C-122 | NHC(O)NH-c-C₃H₅ |
| C-123 | NHC(O)NH-(1-CN-c-C₃H₄) |
| C-124 | NHC(O)NHCH₂-c-C₃H₅ |
| C-125 | NHC(O)NHCH₂-(1-CN-c-C₃H₄) |
| C-126 | CH=N—OCH₃ |
| C-127 | CH=N—OCH₂CH₃ |
| C-128 | CH=N—OCH₂CHF₂ |
| C-129 | CH=N—OCH₂CF₃ |
| C-130 | CH=N—OCH₂CH=CH₂ |
| C-131 | CH=N—OCH₂C≡CH |
| C-132 | CH=N—OCH₂CN |
| C-133 | CH=N—O-c-C₃H₅ |
| C-134 | CH=N—O-(1-CN-c-C₃H₄) |
| C-135 | CH=N—O-(2,2-F₂-c-C₃H₃) |
| C-136 | CH=N—O—CH₂-c-C₃H₅ |
| C-137 | CH=N—O—CH₂-(1-CN-c-C₃H₄) |
| C-138 | CH=N—O—CH₂-(2,2-F₂-c-C₃H₃) |

C-3 is a particularly preferred embodiment.

EXAMPLES

A. Preparation Examples

With appropriate modification of the starting materials, the procedures given in the synthesis description were used to obtain further compounds I. The compounds obtained in this manner are listed in the table that follows, together with physical data.

The products shown below were characterized by melting point determination, by NMR spectroscopy or by the masses ([m/z]) or retention time (RT; [min.]) determined by HPLC-MS or HPLC spectrometry.

HPLC-MS=high performance liquid chromatography-coupled mass spectrometry;

HPLC method 1: Phenomenex Kinetex 1.7 µm XB-C18 100 A; 50×2.1 mm; mobile phase: A: water+0.1% trifluoroacetic acid (TFA); B: acetonitrile; gradient: 5-100% B in 1.50 minutes; 100% B 0.25 min; flow: 0.8-1.0 ml/min in 1.51 minutes at 60° C. MS: ESI positive, m/z 100-700.

Example 1: Preparation of 4-amino-5-chloro-2,3-dihydrobenzofuran-7-carboxamide (Compound 1)

To a solution of 150 g 4-amino-5-chloro-2,3-dihydrobenzofuran-7-carboxylic acid in 600 ml DMF at 70° C. was added a warm solution of 113.85 g carbonyl diimidazole in 400 ml DMF dropwise. After addition was complete, the reaction was stirred at 70° C. for 2.5 hours then, 330 mL 25% aqueous NH₃ solution was added dropwise. When the addition was complete the reaction was stirred for 2 hours at 70° C., allowed to cool to 20-25° C. and stirred for 18 hours. The reaction was then poured into 1.2 L of water at 20-25° C. while stirring, and stirred for 15 minutes. The precipitated solid was isolated by filtration, and washed with water, and dried in vacuo at 50° C. to afford the title compound as a white solid (127.75 g, 86% yield).

LC-MS: [M]⁺ 213.0; $t_R$=0.655 min.

Example 2: Preparation of 4-amino-5-chloro-2,3-dihydrobenzofuran-7-carbonitrile (Compound 2)

A solution of 70.5 g Compound 1 in 206 mL POCl₃ was heated to 80° C. for 1.5 hours. The reaction was then cooled to be 35° C. and 170 mL toluene was added. The reaction was then further cooled to 0° C. and stirred at 0° C. for 15 minutes. The precipitated solid was then collected by filtration and washed with toluene. The filtercake was then slurried in 500 mL water at 0° C., stirred for 15 minutes, and filtered. The filter cake was then washed with water, and then dried in vacuo at 50° C. to afford the title compound as a white solid (44.42 g, 69% yield).

LC-MS: [M]+194.9; $t_R$=0.900 min.

Example 3: Preparation of 4-amino-2,3-dihydrobenzofuran-7-carbonitrile (Compound 3)

To a solution of 50 g Compound 2 in 950 mL ethanol and 14 mL acetic acid at 20-25° C. was added 13.6 g 10% wt Pd/C portionwise. The reaction was then warmed to 70° C. and a solution of 42.7 g potassium formate in 50 mL water was added dropwise. After completion of the addition, the reaction was stirred 10 minutes at 70° C. until gas evolution ceased. During the addition, the reaction temperature increased to 78° C. The reaction was then cooled to 50° C. and filtered, and the filtercake washed with 450 mL of 50° C. ethanol. The filtrate was then concentrated in vacuo to afford a residue. To the residue was added 600 mL water, and the resulting suspension was stirred vigorously at 0° C. for 1 hour. The suspension was then filtered, and the filtercake washed with water, then dried in vacuo at 50° C. to afford the title compound as a white solid (33.6 g, 82% yield).

LC-MS: [M]⁺ 161.1; $t_R$=0.715 min.

Example 4: Preparation of 4-bromo-2,3-dihydrobenzofuran-7-carbonitrile (Compound 4)

To a solution of 54.6 g Compound 3 in 930 mL acetonitrile was added 75.4 g CuBr portionwise. The reaction was then warmed to 40° C. and a solution of 56.7 g t-butyl nitrite in 110 mL acetonitrile was added over 40 minutes. The reaction was then stirred at 40° C. for 5 hours, allowed to cool to 20-25° C. and stir at 20-25° C. for 15 hours. The reaction was then poured into 2.5 L of stirring ice water and stirred an additional 30 minutes. The resulting slurry was then filtered and the filtercake was washed with water, and then dissolved in 1.4 L CH₂Cl₂. To the CH₂Cl₂ solution was added 430 g Na₂SO₄ and the suspension was stirred vigorously for 1 hour. The suspension was then filtered, washed with CH₂Cl₂ and concentrated in vacuo to afford a light brown solid which was carried on without further purification (52.3 g, 68% yield).

LC-MS: [M]⁺ 223.9; $t_R$=1.048 min.

Example 5: Preparation of 4-acetyl-2,3-dihydrobenzofuran-7-carbonitrile (Compound 5)

To a solution of 14.2 g Compound 4 in 500 mL toluene was added sequentially 25 g tributyl(1-ethoxyvinyl)tin and 3.40 g [1,1'-Bis(diphenylphosphino)ferrocene]dichloropalladium(II). The reaction was then heated to 120° C. and stirred for stirred for 18 hours. The reaction was then cooled to 20-25° C., 500 mL water was added, layers separated and the aqueous layer extracted with $CH_2Cl_2$. The combined organics are cooled to 0° C. and 330 mL 6 M HCl was added while stirring, the biphasic mixture is then stirred vigorously for 2 hours at 20-25° C. Layers were then separated, and the aqueous layer extracted with toluene. The combined organic phases were then washed with 10% aqueous $K_2CO_3$ solution, dried, filtered and concentrated in vacuo to afford a residue which was purified via flash chromatography using a 1:9 mixture of $K_2CO_3$:silica gel as a solid phase, eluting with 100% $CH_2Cl_2$ to afford the title compound as an off-white solid (12.1 g, 65% yield).

LC-MS: $[M]^+$ 188.1; $t_R$=0.895 min.

Example 6: Preparation of 4-acetyl-2,3-dihydrobenzofuran-7-carbonitrile (Compound 5)

To a solution of 30.0 g Compound 4 in 300 mL methanol was sequentially added 69.3 g 1,4-butane diol vinyl ether, 1.80 g palladium acetate, 5.52 g (1,3-Bis(diphenylphosphino)propane), and 31.2 g powdered $Na_2CO_3$. The reaction was then heated to 65° C. for 18 hours, then cooled to 20-25° C., filtered, and filtercake washed with methanol and concentrated in vacuo to volume of 150 mL. The solution was then cooled to 0° C., and 105 mL 6 M HCl was added dropwise. During the addition of HCl a solid precipitates, and 200 mL MeOH was added. After addition of HCl was complete, the mixture was stirred for 30 minutes, filtered, the filtercake washed with water, and then dried in vacuum at 50° C. to afford the desired product as a white solid (23.5 g, 93% yield).

LC-MS: $[M]^+$ 188.1; $t_R$=0.895 min.

Example 7: Preparation of N-[(4-acetyl-2,3-dihydrobenzofuran-7-yl)methyl]propanamide (Compound 6)

To a solution of 14.8 g Compound 5 in 720 mL THF at 20-25° C. is added sequentially a solution of 26.8 g $NaHCO_3$ in 340 mL water, 31.3 g propropionic anhydride and 63.0 g 50% (suspension in water) Raney Nickel. The reaction was then stirred under an atmosphere of hydrogen at 20-25° C. for 5 hours. The reaction was then filtered and the filtercake was washed with 2:1 $THF:H_2O$. THF was then removed in vacuo and an additional 200 mL water was then added to the suspension. The solid was removed by filtration, washed with water and then dried in vacuum at 50° C. to afford a crude product. The product was then suspended in 80 mL ethylacetate (EtOAc), cooled to 0° C., and the solid removed by filtration. The filtercake was washed with minimal EtOAc and then dried in a vacuum oven at 50° C. to afford the title compound as a white solid (13.7 g, 70% yield).

LC-MS: $[M]^+$ 248.1; $t_R$=0.783 min.

Example 8: Preparation of N-[[4-[(Z)-3-(3,5-dichloro-4-fluoro-phenyl)-4,4,4-trifluoro-but-2-enoyl]-2,3-dihydrobenzofuran-7-yl]methyl]propanamide (Compound 7)

To a suspension of 43.7 g Compound 6 and 55.0 g $Cs_2CO_3$ in 320 mL toluene and 320 mL trifluorotoluene at 115° C. was added 60.4 g 1-(3,5-dichloro-4-fluoro-phenyl)-2,2,2-trifluoroethanone dropwise over 2 hours. The reaction was then heated at 115° C. for an additional 18 hours, then cooled to 20-25° C. and concentrated in vacuo to afford a brown solid. The solid was slurried in water and stirred vigorously for 1 hour, cooled to 0° C., and filtered. The filtercake was then tritrated with 500 mL MTBE, filtered, and the filtercake then dried in a vacuum oven at 50° C. to afford the title compound as a light brown solid (72.1 g, 75% yield).

LC-MS: $[M]^+$ 490.0; $t_R$=1.291 min.

Example 9: Preparation of N-[[4-[5-(3,5-dichloro-4-fluoro-phenyl)-5-(trifluoromethyl)-4H-isoxazol-3-yl]-2,3-dihydrobenzofuran-7-yl]methyl]propanamide (Compound 8)

To a suspension of 101 g Compound 7 in 500 mL MeOH was added a warm solution of 18.7 g hydroxylamine HCl in 100 mL MeOH over 10 minutes. The reaction was then stirred at 20-25° C. for 1 hour after the addition was complete. Then a solution of 19.0 g NaOH in 160 mL MeOH was added dropwise over 40 minutes. The reaction was then stirred for 18 hours at 20-25° C. Then the reaction was poured into stirring solution of 4 L ice water and 150 mL of conc. HCl, and stirred for 1 hour. The precipitated solid is collected by filtration, washed with water, dissolved in $CH_2Cl_2$ and washed with aqueous 1 M HCl, dried over $Na_2SO_4$ and concentrated in vacuo to afford a light brown solid which was purified by silica gel chromatography eluting with 5-10% acetone/in $CH_2Cl_2$ to afford the title compound as a white solid (120 g, 97% yield).

LC-MS: $[M]^+$505.0; $t_R$=1.337 min.

The invention claimed is:
1. A compound of formula I which corresponds to formula IA

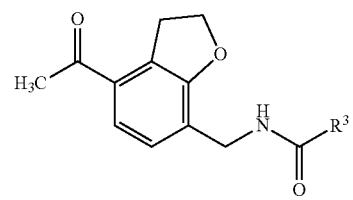

IA wherein
R$^3$ is H, $C_1$-$C_6$-alkyl, $C_1$-$C_6$-haloalkyl, wherein the carbon chains may be substituted with one or more R$^{31}$; $C_1$-$C_6$-alkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl which is unsubstituted or substituted with CN, $C_3$-$C_6$-halocycloalkyl, N(R$^{5a}$)R$^{5b}$, C(=O)N(R$^{5a}$)R$^{5b}$, CH=NOR$^4$, phenyl, or a 4-, 5-, or 6-membered saturated, partially or fully unsaturated heterocyclic ring (HET) comprising 1, 2 or 3 heteroatoms N, O, and/or S as ring members, which rings are unsubstituted or partially or fully substituted by same or different R$^{32}$, R$^{31}$ is OH, CN, $C_3$-$C_6$-cycloalkyl unsubstituted or substituted with CN or halo-methyl, $C_3$-$C_6$-halocycloalkyl, $C_1$-$C_6$-alkoxy, $C_1$-$C_6$-haloalkoxy, SO$_n$—$C_1$-$C_6$-alkyl, SO$_n$—$C_1$-$C_6$-haloalkyl, C(=O)N(R$^{5a}$)R$^{5b}$, phenyl, or a 4-, 5-, or 6-membered saturated, partially or fully unsaturated heterocyclic ring (HET) comprising 1, 2 or 3 heteroatoms N, O, and/or S as ring members, which rings are unsubstituted or partially or fully substituted with same or different R$^{32}$;

$R^{32}$ is halogen, CN, $NO_2$, $C_1$-$C_4$-haloalkyl, $C_2$-$C_4$-alkenyl, $C_2$-$C^4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $SO_n$—$C_1$-$C_4$-alkyl, $SO_n$—$C_1$-$C_4$-haloalkyl, $C_1$-$C_4$-alkylcarbonyl, $C_1$-$C_4$-haloalkylcarbonyl, aminocarbonyl, $C_1$-$C_4$-alkylaminocarbonyl, and di-($C_1$-$C_4$-alkyl)amino-carbonyl; or two $R^{32}$ present on the same carbon atom of a saturated ring may form together =O or =S; or two $R^{32}$ present on the same S or SO ring member of a heterocycle may together form a group =N($C_1$-$C_6$-alkyl), =NO($C_1$-$C_6$-alkyl), =NN(H)($C_1$-C6-alkyl) or =NN($C_1$-$C_6$-alkyl)$_2$, $R^4$ is H, $C_1$-$C_6$-alkyl, or $C_1$-$C_6$-haloalkyl;

$R^{5a}$ is H, or $C_1$-$C_6$-alkyl;

$R^{5b}$ is H, $C_1$-$C_6$-alkyl, $C_1$-$C_6$-haloalkyl, $C_2$-$C_4$-alkenyl, $C_2$-$C_4$-alkynyl, $CH_2CN$, $C_3$-$C_6$-cycloalkyl, $C_3$-$C_6$-halocycloalkyl, $C_3$-$C_6$-cycloalkylmethyl, $C_3$-$C_6$-halocycloalkylmethyl, phenyl, heterocycle HET which rings are unsubstituted, or partially or fully substituted with same or different $R^{32}$; and each n is independently 0, 1, or 2.

2. The compound of formula I according to claim 1 wherein $R^3$ is $C_1$-$C_6$-alkyl.

3. The compound of formula I according to claim 1 wherein $R^3$ is ethyl.

4. A process for preparing the compound of formula IA according to claim 1, the process comprising:

performing reductive amidation of a nitrile of formula II

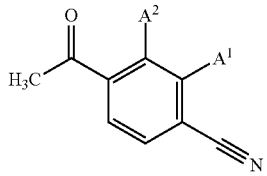

II wherein $A^1$ and $A^2$ together form a chain $-(CH$_2$)$_2$—O-#, wherein # is the bond to position $A^1$ and $ is the bond to position $A^2$, with an activated carbonyl compound of formula III,

III wherein $R^3$ is the same as defined formula IA, and Y is a nucleophilic leaving group, and which nitrile is obtained by reaction of a compound of formula IV

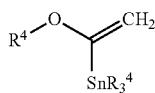

IV with a halogen compound of formula V,

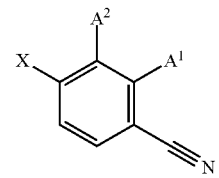

V wherein X is a halogen atom, which halogen compound V in turn is obtained by Sandmeyer reaction of an aniline derivative of formula VI

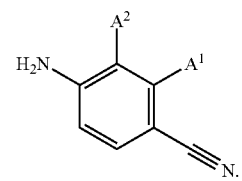

VI

5. The process according to claim 4, which further comprises preparation of the aniline derivative of formula VI by reductive dehalogenation of the chloro compound of formula VII

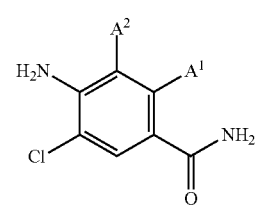

VII which can be prepared from an amide of formula VII

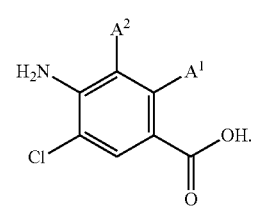

VIII which can be prepared by amidation of the corresponding benzoic acid of formula IX

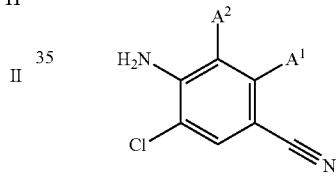

IX

6. The process according to claim 4, wherein $R^3$ is $C_1$-$C_6$-alkyl.

\* \* \* \* \*